US010231911B2

(12) United States Patent
Dersh et al.

(10) Patent No.: US 10,231,911 B2
(45) Date of Patent: *Mar. 19, 2019

(54) METHOD AND COMPOSITION FOR TREATING SKIN CONDITIONS (71) Applicant: L'OREAL, Paris (FR)

(72) Inventors: Justin Dersh, Clark, NJ (US); Geoffrey Genesky, Clark, NJ (US); Jodi Goldberg, Clark, NJ (US); Valerie Robert, Clark, NJ (US); Victoria Fu, Clark, NJ (US); Carol Elmasry, South Amboy, NJ (US)

(73) Assignee: L'Oreal, Paris (FR)

(*) Notice: Subject to any disclaimer, the term of this patent is extended or adjusted under 35 U.S.C. 154(b) by 0 days.

This patent is subject to a terminal disclaimer.

(21) Appl. No.: 15/251,740

(22) Filed: Aug. 30, 2016

(65) Prior Publication Data

US 2017/0281492 A1    Oct. 5, 2017

Related U.S. Application Data (60) Provisional application No. 62/316,334, filed on Mar. 31, 2016.

(51) Int. Cl.
*A61K 31/74* (2006.01)
*A61K 31/01* (2006.01)
*A61K 8/31* (2006.01)
*A61K 8/368* (2006.01)
*A61K 8/34* (2006.01)
*A61K 8/92* (2006.01)
*A61K 8/97* (2017.01)
*A61K 8/37* (2006.01)
*A61K 8/67* (2006.01)
*A61Q 19/08* (2006.01)
*A61B 5/00* (2006.01)

(52) U.S. Cl.
CPC .............. *A61K 8/31* (2013.01); *A61B 5/442* (2013.01); *A61K 8/347* (2013.01); *A61K 8/368* (2013.01); *A61K 8/37* (2013.01); *A61K 8/671* (2013.01); *A61K 8/676* (2013.01); *A61K 8/922* (2013.01); *A61K 8/97* (2013.01); *A61Q 19/08* (2013.01); *A61K 2800/87* (2013.01)

(58) Field of Classification Search
None
See application file for complete search history.

(56) References Cited

U.S. PATENT DOCUMENTS

| 4,595,586 | A | * | 6/1986 | Flom | A61K 8/342 |
| | | | | | 424/47 |
| 6,524,598 | B2 | | 2/2003 | Sunkel et al. | |
| 7,349,857 | B2 | | 3/2008 | Manzo | |
| 8,034,755 | B2 | | 10/2011 | Kawano | |
| 9,442,494 | B2 | | 9/2016 | Igarashi | |
| 2007/0082017 | A1 | | 4/2007 | Tseng | |
| 2008/0243523 | A1 | | 10/2008 | Beilis | |
| 2009/0022826 | A1 | * | 1/2009 | Shrier | A61K 9/0014 |
| | | | | | 424/754 |
| 2009/0263340 | A1 | * | 10/2009 | Ille-Boehler | A61K 8/368 |
| | | | | | 424/62 |
| 2011/0158922 | A1 | * | 6/2011 | Dupont | A61K 8/73 |
| | | | | | 424/59 |
| 2011/0305737 | A1 | | 12/2011 | Alexiades-Armenakas | |
| 2015/0021356 | A1 | | 1/2015 | Witchell et al. | |

FOREIGN PATENT DOCUMENTS

| EP | 0443741 A1 | 8/1991 |
| WO | 0064570 A1 | 11/2000 |
| WO | 2009137277 A3 | 11/2009 |
| WO | 2010104687 A2 | 9/2010 |
| WO | 2013113856 A1 | 8/2013 |
| WO | 2014095204 A2 | 6/2014 |
| WO | 2015111002 A1 | 7/2015 |

OTHER PUBLICATIONS https://www.ricaud.com/en/beauty-advice/facial-care-diagnosis.htm Pierre Ricaud (downloaded from the Internet Jun. 13, 2017).
https://www.codageparis.com/en/myscan/index/step0/ Codage Paris (downloaded from the Internet Jun. 13, 2017).
Mintel, White White Beauties; XP-002770906; http://www.gnpd.com, Published Jul. 2011.
International Search Report and Written Opinion of the International Searching Authority for International Application No. PCT/US2017/025412 dated Jun. 26, 2017.
International Search Report for PTC/US2018/025111 dated Jun. 22, 2018.

* cited by examiner

*Primary Examiner* — Jeffrey T. Palenik
(74) *Attorney, Agent, or Firm* — McNees Wallace & Nurick LLC (57) ABSTRACT An oil base skin care composition including squalane and a method for treating skin are disclosed. The method includes the step of individually displaying a plurality of visual skin guides to a consumer. Each of the visual skin guides includes a plurality of visual representations of a categorical skin condition. Each of the visual representations correspond to a severity score for the categorical skin condition on the visual skin guide. The method further includes correlating the severity score for each of the categorical skin conditions for each of the visual skin guides to the consumer's current skin condition. At least two target skin conditions from the plurality of categorical skin conditions are determined in response to the severity scores for each of the categorical skin conditions. At least one booster containing at least one active ingredient is correlated for treating each target skin condition.

32 Claims, 3 Drawing Sheets

METHOD AND COMPOSITION FOR TREATING SKIN CONDITIONS

CROSS-REFERENCE TO RELATED APPLICATIONS

This patent application claims the benefit of U.S. Provisional Patent Application Ser. No. 62/316,334 filed on Mar. 31, 2016 and entitled "Method and Composition for Treating Skin Conditions", the disclosure of which is hereby incorporated by reference herein in its entirety and made part of the present U.S. utility patent application for all purposes.

FIELD OF THE INVENTION

The present invention is directed to a skin care composition and a method for treating skin conditions. More specifically, the present invention is directed to a skin care composition that has targeted active ingredients for treating target skin conditions and methods for creating customized skin care compositions.

BACKGROUND OF THE INVENTION

Personalized skin care systems are desirable for consumers to provide a skin care composition that meets the skin care needs of the individual consumer.

Known personalized product lines include MaCrèmeSurMesure by Dr. Pierre Ricaud, Codage Paris, Customized TCM by Yue Sai, and prescription personalized serums (Re-Plasty) by Helena Rubinstein.

Helena Rubinstein uses a skinprofiler, a cutaneous analysis device that generates quantitative data to analyze a variety of skin attributes to diagnose consumers in-store and provide them with a personalized prescription product consisting of one universal serum base and single dose of concentrate. Helena Rubenstein products only consist of one single dose of concentrate containing actives that seek to address all skincare needs. In addition, the Helena Rubenstein product is a serum (aqueous based) product with water-soluble actives. The Helena Rubinstein skinprofiler measures elasticity, pigmentation, and texture of the skin and prescribes concentrate based on these results only.

Codage Paris has a custom-made skincare product line. Consumers use a website diagnostic tool in which they answer 23 questions that were developed by different specialists (including dermatologists, pharmacists, and nutritionists). Based on the results, Codage selects and formulates a composition in their existing line and sends consumers a final product within a week. The Codage Paris system does not include a base composition with personalized boosters. Codage Paris is a serum (aqueous based) product with water soluble actives. A diagnostic tool utilized for Codage is an online survey which automatically 'prescribes' a final product based on provided answers. The Codage Product provides a final pre-prepared formula for the consumer, which is sent directly from store to consumer, wherein no mixing is required.

MaCrèmeSurMesure by Dr. Pierre Ricaud similarly uses an online diagnostic tool in which consumers are given a questionnaire on their current skin and lifestyle. Based on the answers they provide, the website provides them with a cream base and combination of three active concentrates. Each "concentrate" for the MaCrèmeSurMesure only contains a single active ingredient. Typical "concentrates" for the MaCrèmeSurMesure products consist solely of pure extracts (100% active extract of chufa tubers, for example) and do not provide formulations. The MaCrèmeSurMesure product is aqueous based (water based moisturizing gel texture) and booster "concentrates" are water soluble extracts in aqueous form. The consumer is sent a kit with their products and mixes at home with a small mixing tool provided, which is not easily co-soluble. MaCrèmeSurMesure uses an online questionnaire to diagnose consumer.

Yue Sai is a Customized TCM Beauty Solution Ultimate Refining Serum that includes in-store formulations in China. The tailoring of the formulations were limited and included only aqueous based compositions.

There remains a need to provide an effective, targeted anhydrous oil based skin care composition and method for treating skin that is customized to specific, individual customer target skin compositions and is readily dispersible.

BRIEF SUMMARY OF THE INVENTION

In an exemplary embodiment, a method for treating skin including the step of individually displaying a plurality of visual skin guides to a consumer. Each of the visual skin guides includes a plurality of visual representations of a categorical skin condition. Each of the visual representations correspond to a severity score for the categorical skin condition on the visual skin guide. The method further includes correlating the severity score for each of the categorical skin conditions for each of the visual skin guides to the consumer's current skin condition. At least two target skin conditions from the plurality of categorical skin conditions are determined in response to the severity scores for each of the categorical skin conditions. At least one booster containing at least one active ingredient for treating is correlated to each target skin condition In addition, an oil base formulation including squalane is provided. The booster compositions and oil base formulations are individually packaged and the booster compositions are readily dispersible in the oil base formulation.

In another exemplary embodiment, a skin care system having a base oil composition including squalane and a plurality of booster compositions readily dispersible into the base oil composition and comprising corresponding active ingredients. The corresponding active ingredients being ingredients that correspond to treatment skin conditions determined by a consumer. The system includes packaging comprising separate containers for each of the booster compositions and the base oil composition.

The present disclosure is also directed to a method for cosmetic treatment of skin by applying the above-disclosed composition onto a surface of the skin.

Other features and advantages of the present invention will be apparent from the following more detailed description of the preferred embodiment which illustrates, by way of example, the principles of the invention.

BRIEF DESCRIPTION OF THE DRAWINGS

Wherever possible, the same reference numbers will be used throughout the drawings to represent the same parts.

DETAILED DESCRIPTION OF THE INVENTION

All numbers expressing quantities of ingredients and/or reaction conditions are to be understood as being modified in all instances by the term "about", unless otherwise indicated.

"Keratinous tissue," as used herein, includes, but is not limited to, skin, hair, and nails.

"Homogenous" means having the visual appearance of being substantially uniform throughout, i.e., visually appears as a single phase.

The method and system, according to the present disclosure, includes a method wherein a comprehensive assisted in-store target skin condition diagnosis practice with a targeted and efficacious product that is mixed at the consumer's home in order to use. An assisted or unassisted skin diagnosis/questionnaire, using visual aids, is completed to provide targeted skin care system to address the individual customer's needs. In one embodiment, consumers are shown representative photos of common skin conditions, wherein the consumers view the visual aids and correlate the visual aids with their individual skin care needs. Based on the correlation to the target skin conditions, the consumers get a customized skin care system having a base oil composition and two selected active booster compositions, which the consumer mixes at home.

Method

Figure 1:
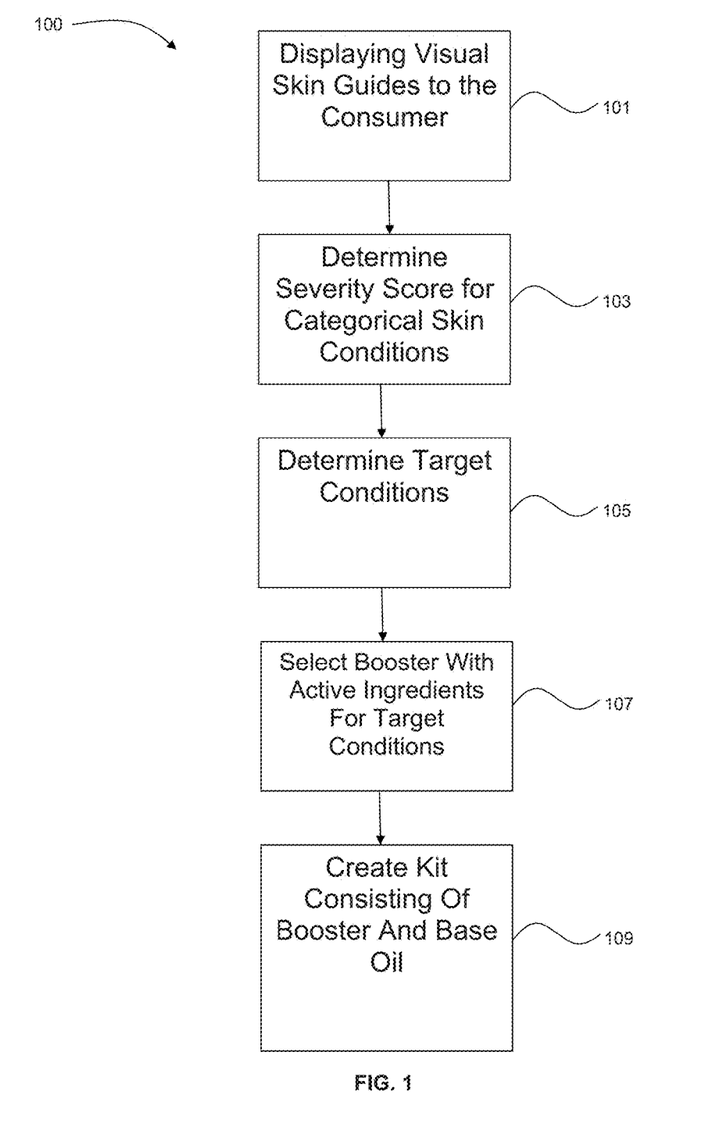
FIG. 1 shows a method, according to an embodiment of the present disclosure.
Figure 2:
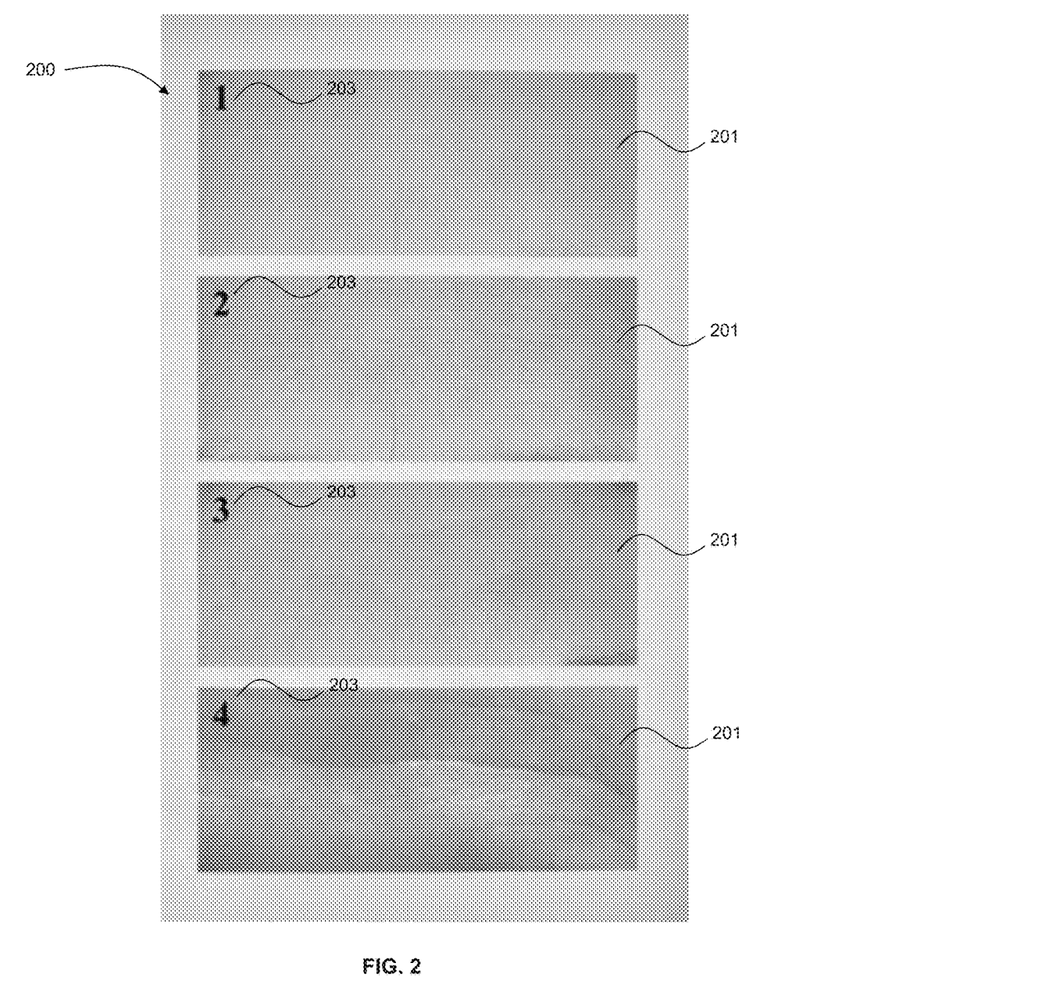
FIG. 2 is a visual skin guide, according to an embodiment of the present disclosure.

FIG. 1 shows a method 100, according to the present disclosure. Method 100 includes individually displaying a plurality of visual skin guides 200 to a consumer (step 101). FIG. 2 shows an exemplary visual skin guide for skin wrinkles. Although FIG. 2 shows an example of visual skin guide, the present invention is not so limited and may include other types of visual displays or other categorical skin conditions. Other suitable types of visual displays include, but are not limited to, books, brochures and pamphlets including, but not limited to, pictures and/or description of skin condition and scale, clinical pictures, and photos taken with instrumental devices. The pictures and/or photos may include representations of skin conditions for panelists of different ethnicities and skin types. The visual display will correspond to the varying ethnicities and skin types. A selection of a specific visual display is made to consumer's ethnicity and/or skin types. The visual skin guide 200 is a device including visual representations 201, including, but not limited to, images, pictorial representations or similar visual devices that provide information regarding categorical skin conditions. In one embodiment, as shown in FIG. 2, each of the visual skin guides includes a plurality of visual representations of a categorical skin condition. In this embodiment, each of the visual representations correspond to a severity score 203 for the categorical skin condition on the visual skin guide. The method includes determining the severity score 203 from the visual skin guides 200, (step 103). For example, the visual representations may include photographs showing a particular category of skin condition of the categorical skin conditions including, but not limited to, skin brightness, skin lines/wrinkles, visibility of pores, skin texture, skin redness, skin firmness, skin tone evenness with a score that corresponds to severity. The severity score 203 may be a numerical value, grade value or any other suitable scoring that permits the comparison of the categorical skin conditions. In one embodiment, the visual skin guide 200 includes four photographs of a particular skin condition scored numerically, for example, from 1 to 3 or from 1 to 4 or from 1 to 5 or from 1 to 10 or from 1 to 20 or from 1 to 100.

The method 100 further includes correlating the severity score 203 for each of the categorical skin conditions for each of the visual skin guides to the consumer's current skin condition. The correlating includes comparing the severity scores of each of the categorical skin conditions and determining a plurality of target skin conditions for treatment (step 105). The correlation may include a comparison of the numerical value, grade or other value indicator for the severity of the skin condition to determine which skin conditions are suitable for treatment. In other embodiments, the correlation may include a consultation with a skin care professional, who may assist the consumer in determining the severity score or may assist in comparing the severity score in determining the target skin conditions. At least two target skin conditions are determined from the plurality of categorical skin conditions in response to the severity scores for each of the categorical skin conditions with or without consultation with a skin care professional.

In the embodiment, wherein consultation from a skin care professional is utilized, consultation time of about 20 minutes with consumer has been determined to be beneficial. The skin care consultant may provide direction relating to the consumer's current regimen, skin type, skin concerns and lifestyle. To assess top skin concerns, diagnostic tools which may include, but is not limited to, a combination of a special prescription card (ranking of concerns) and reference pictures (skin atlas) are utilized.

As shown in FIG. 1, after the target skin conditions are determined, boosters with at least one active ingredient are correlated for each of the target skin conditions (step 107). The boosters that are selected for the target skin conditions are selected based upon active ingredients that provide improvement in the target skin condition. For example, in one embodiment, the boosters containing active ingredients correlating to target conditions are selected as compositions that are capable of treating conditions selected from skin brightness, skin wrinkles, visibility of pores, skin texture, skin redness, skin firmness, and skin tone evenness. After the boosters are selected, a kit including the selected booster and base oil are created or assembled (step 109).

Brightening Booster Composition

In one embodiment, the target skin condition determined for treatment is skin brightness. The active ingredient corresponding to skin brightness includes one or more actives that provide improvement to skin brightness. In one embodiment, at least 25% or from about 25% to about 40% or from about 28% to about 35%, about 26%, about 30%, about 34%, or about 38%, by weight of the brightening booster active for skin brightness is included in the brightening booster composition. For example, in one embodiment, the actives corresponding to the skin brightness include one or more of ascorbyl tetraisopalmitate, phenylethyl resorcinol, arbutin, *eperua falcata* bark extract, ceramides, punica granatum fruit extract, citrus aurantium *dulcis* (orange) peel essential oil, rapeseed oil, *cassia alata* leaf extract, purple rice extract, other components that provide improvement to skin brightness, any other suitable soluble/dispersible targeted active ingredient, and combinations thereof. In one embodiment, the active ingredients in the booster composition corresponding to skin brightness include greater than about 27% or from about 28% to about 34% or from about 29% to 31%, about 28%, about 30%, about 32%, or about 34% by weight of the brightening booster composition ascorbyl tetraisopalmitate, and greater than about 1% or from about 1% to about 5% or from about 2% to 3.5%, about 1%, about 2%, about 3%, or about 4%, by weight of the brightening booster composition phenylethyl resorcinol.

Pore Minimizing Booster Composition

In one embodiment, the target skin condition determined for treatment is visibility of pores. The active ingredient corresponding to skin brightness includes one or more actives that provide improvement to visibility of pores. In one embodiment, at least 25% or from about 25% to about 40% or from about 28% to about 35%, about 25%, about 28%, about 31%, about 33%, about 36% or about 39% by weight of the pore minimizing active for pore minimizing is included in the brightening booster composition. For example, in one embodiment, the actives corresponding to the visibility of pores include one or more of ascorbyl tetraisopalmitate, salicylic acid, crithimum maritimum extract, totarol, ulkenia amoeboidea oil, other components that provide improvement to visibility of pores, any other suitable soluble/dispersible targeted active ingredient, and combinations thereof. In one embodiment, the active ingredients in the booster composition corresponding to visibility of pores include greater than about 27% or from about 28% to about 34% or from about 29% to 31%, about 28%, about 30%, about 32%, or about 34% by weight of the pore minimizing booster composition ascorbyl tetraisopalmitate, greater than about 0.5% or from about 0.75% to about 2.0% or from about 1.0% to 1.5%, about 1.1%, about 1.2%, about 1.3%, or about 1.4% by weight of the pore minimizing booster composition salicylic acid, and greater than about 0.25% or from about 0.05% to about 0.25% or from about 0.07% to 0.15% or about 0.10%, about 0.11%, about 0.13%, or about 0.14% by weight of the pore minimizing booster composition about crithimum maritimum extract, based upon the weight of the booster composition.

Texture Refining Booster Composition

In one embodiment, the target skin condition determined for treatment is texture refining. The active ingredient corresponding to texture refining includes one or more actives that provide improvement to skin texture. In one embodiment, the active ingredients in the booster composition corresponding to texture refining include greater than about 7.5% or from about 10% to about 20% or from about 11% to about 14%, about 10%, about 12%, about 14%, about 16%, about 18%, or about 20% by weight of the texture refining booster composition. For example, in one embodiment, the actives corresponding to skin texture include one or more of glyceryl linoleate (and) glyceryl oleate (and) glyceryl linolenate, punica granatum fruit extract, shea butter, rice bran oil, safflower oil, phospholipids, panax ginseng root extract, other components that provide improvement to skin texture, any other suitable soluble/dispersible targeted active ingredient, and combinations thereof. In one embodiment, the active ingredients in the booster composition corresponding to skin texture include greater than about 7.5% or from about 10% to about 20% or from about 11% to about 14%, about 10%, about 12%, about 14%, about 16%, about 18% or about 20% by weight of the texture refining booster composition glyceryl linoleate (and) glyceryl oleate (and) glyceryl linolenate.

Visible Redness Booster Composition

In one embodiment, the target skin condition determined for treatment is visible redness. The active ingredient corresponding to visible redness includes one or more actives that provide improvement to the skin redness. In one embodiment, the active ingredients in the booster composition corresponding to visible redness include greater than about 7.5% or from about 10% to about 20% or from about 11% to 14%, about 10%, about 12%, about 14%, about 16%, about 18% or about 20% by weight of the visible redness booster composition. For example, in one embodiment, the actives corresponding to the skin texture include one or more of helianthus annuus (sunflower) seed oil unsaponifiables, melissa officinalis leaf oil, zingiber officinale (ginger) root oil, anthemis nobilis flower oil, other components that provide improvement to skin redness, any other suitable soluble/dispersible targeted active ingredient, and combinations thereof. In one embodiment, the active ingredients in the booster composition corresponding to skin redness include at least one active ingredient corresponding to skin redness include greater than about 7.5% or from about 10% to about 20% or from about 11% to 14%, about 12%, about 14%, about 16%, about 18%, or about 20% by weight of the visible redness booster composition helianthus annuus (sunflower) seed oil unsaponifiables, based upon the weight of the booster composition.

Wrinkle Reducing Booster Composition

In one embodiment, the target skin condition determined for treatment is skin wrinkles. The active ingredient corresponding to wrinkle reducing includes one or more actives that provide improvement to the skin wrinkles. For example, in one embodiment, the actives corresponding to the skin wrinkles include at least one active ingredient selected from the group consisting of retinol, retinyl palmitate, punica granatum fruit extract, pelargonium graveolens flower oil, melissa officinalis leaf oil, zingiber officinale (ginger) root oil, theobroma cacao (cocoa) extract, purple rice extract, phytosphingosine, cinnamic acid, other components that provide improvement to skin wrinkles, any other suitable soluble/dispersible targeted active ingredient, and combinations thereof. In one embodiment, the active ingredients in the booster composition corresponding to wrinkle reduction include greater than about 0.5% or from about 1.0% to about 3.0% or from about 1.5% to 2.0%, about 1.0%, about 1.5%, about 2.0%, about 2.5%, or about 3.0% by weight of the wrinkle reducing booster composition. In one embodiment, the active ingredients in the booster composition corresponding to skin wrinkles include at least one active ingredient corresponding to skin wrinkles include greater than about 0.25% or from about 0.5% to about 1.5% or from about 0.75% to 1.00% about 0.5%, about 0.7%, about 0.9%, about 1.1%, about 1.3% or about 1.5% by weight of the wrinkle reducing booster composition retinol, and greater than about 0.25% or from about 0.5% to about 1.5% or from about 0.75% to 1.00%, about 0.5%, about 0.7%, about 0.9%, about 1.1%, about 1.3% or about 1.5%, by weight of the wrinkle reducing booster composition retinyl palmitate, based upon the weight of the booster composition.

Booster Additives

The booster compositions noted above may further include additional additives. For example, the booster compositions may include essential oils, Vitamin E, emollients or other ingredients for skin enhancement, solubilization or other beneficial or efficacious purpose. In one embodiment, for example, the booster compositions may include squalane for moisturization, capryloyl salicylic acid for cell turnover and/or botanical oils for skin conditioning.

Base Oil Composition

In addition to the plurality of booster compositions, a base oil composition is also provided. Each of the base oil and the booster compositions are formulated with an anhydrous oil composition, wherein the composition is preferably devoid of water and water based components. The anhydrous composition is appropriate for custom, tailored skin care kit as the compositions contain no water and therefore less prone to microbiological contamination. The anhydrous oil based base oil composition and booster compositions provide a high affinity to skin due to the oil base and permit beneficial mixing of the desired actives. The base oil includes components suitable for providing skin care benefits, such as moisturization, protection of skin barrier, or other skin benefit. Squalane or botanical oils, for example, in a concentration comprising greater than about 20% or greater than about 25% or greater than about 30% or greater than about 35%, by weight of total composition. In one embodiment, the base oil composition comprises squalane, botanical oil, hexyldecanol, and tocopherol, octyldodecanol, dicaprylyl ether, *zea mays* (corn) oil, *passiflora edulis* seed oil, and/or *oryza sativa* (rice) bran oil. Booster composition and base oil composition are formulated cosoluble for ease of use.

Cosolubilization

The booster compositions described above include the active ingredients noted specifically for the categorical skin condition (e.g., skin brightness, skin wrinkles, visibility of pores, skin texture, and/or skin redness). In addition, the compositions cosolubilize to permit easy dispersion of the booster composition into the base oil composition. In addition to easy dispersion, the system according to the present disclosure ensures rapid homogeneity of the final products after combination of booster and base components by the consumer. In each of the booster compositions, at least one of the ingredients in the base oil composition are included in the booster compositions. For example, in one embodiment, squalane is included in each of the booster compositions. In one particularly advantageous embodiment, greater than about 20% or greater than about 25% or greater than about 30% or greater than about 35%, by weight of total composition squalane is included in each of the booster compositions. Visual assessment may be conducted to ensure cosolubility. For example, cosolubility may be determined by visual determination of incompatibility, immicible components, precipitates or other visual indicators indicating a lack of cosolubility.

Auxiliaries

The composition, according to the invention, may comprise at least one dyestuff chosen especially from pigments, nacres, liposoluble dyes, and mixtures thereof.

The term "pigments" should be understood as meaning white or colored, mineral or organic particles of any shape, which are insoluble in the physiological medium and are intended to color the composition.

The term "nacres" should be understood as meaning iridescent particles of any shape, especially produced by certain molluscs in their shell or else synthesized.

The term "dyes" should be understood as meaning generally organic compounds that are soluble in fatty substances, such as oils.

The pigments may be white or colored, and mineral and/or organic. Among the mineral pigments that may be mentioned are titanium dioxides, optionally surface-treated, zirconium oxide and cerium oxide, and also zinc oxide, iron oxide (black, yellow or red) or chromium oxide, manganese violet, ultramarine blue, chromium hydrate and ferric blue and metal powders, such as aluminum powder or copper powder.

An example that may be mentioned is micronized titanium dioxide powder surface-treated with a silica/aluminum hydroxide/alginic acid mixture, sold under the name MT-100AQ.

Among the organic pigments that may be mentioned are carbon black, pigments of D&C type and lakes based on cochineal carmine or on barium, strontium, calcium or aluminum.

The nacreous pigments may be chosen from white nacreous pigments, such as mica coated with titanium or with bismuth oxychloride, colored nacreous pigments, such as titanium mica coated with iron oxides, titanium mica coated especially with ferric blue or with chromium oxide, titanium mica coated with an organic pigment of the abovementioned type, and also nacreous pigments based on bismuth oxychloride.

The liposoluble dyes are, for example, Sudan red, D&C Red No. 17, D&C Green No. 6, β-carotene, soybean oil, Sudan brown, D&C Yellow No. 11, D&C Violet No. 2, D&C Orange No. 5, quinoline yellow, annatto and bromo acids.

The dyestuffs may be present in an amount of from about 0.01% to about 30%, by weight, such as from about 0.1% to about 20%, by weight, such as from about 0.5% to about 15%, by weight, and most preferably from about 0.5% to about 5%, by weight, relative to the total weight of the composition.

In a known manner, the composition of the invention may also contain adjuvants that are common in cosmetics, such as humectants, preserving agents, antioxidants, complexing agents, solvents, fragrances, bactericides, odor absorbers, vitamins, moisturizers, self-tanning compounds and anti-wrinkle active agents. The amounts of these various adjuvants are those conventionally used in the field under consideration, for example, from 0.01% to 20% of the total weight of the composition. Depending on their nature, these adjuvants may be introduced into the fatty phase and/or into lipid vesicles. In one embodiment, the additives or adjuvants would be added to the booster formulations to functionalize them for specific targeted treatments/needs.

The composition of the present disclosure may also contain cosmetically acceptable additives or adjuvants as well as cosmetic or dermatologic active agents. Representative additives and adjuvants include, for example, oil-soluble or oil-miscible solvents or co-solvents. Suitable examples of additives and adjuvants include, but are not limited to, fatty alcohols, fatty amides, alkylene carbonates, glycols, lower alcohols (e.g. ethanol, propanediol), dispersion enhancing agents, polymers, thickening agents, stabilizers, moisturizers, humectants, colorants, fillers, chelating agents, antioxidants (e.g. BHT, tocopherol), essential oils, fragrances, dyes, neutralizing or pH-adjusting agents (e.g., citric acid, triethylamine (TEA) and sodium hydroxide), preservatives, bactericides, conditioning or softening agents (e.g., panthenol and allantoin), extracts, such as botanical extracts, or any other ingredient commonly used in cosmetics for this type of application. Additives and adjuvants may be present in the compositions in amounts generally ranging from about 0.01% to about 10%, by weight. Examples of cosmetic active agents or dermatological active agents include free-radical scavengers, vitamins (e.g., Vitamin E and derivatives thereof), anti-elastase and anti-collagenase agents, peptides, fatty acid derivatives, steroids, trace elements, extracts of algae and of planktons, enzymes and coenzymes, flavonoids and ceramides, hydroxy acids and mixtures thereof, and enhancing agents. These ingredients may be soluble or dispersible in oil phase(s) that is/are present in the composition.

le;2qOf course, a person skilled in the art will take care to choose this or these optional additional compounds so that the advantageous properties intrinsically attached to the composition, in accordance with the invention, are not, or not substantially, detrimentally affected by the envisaged addition or additions.

Needless to say, a person skilled in the art will take care to select this or of these optional additional compound(s), and/or the amount thereof, such that the advantageous properties of the composition, according to the invention, are not, or are not substantially, adversely affected by the envisaged addition.

Packaging

Figure 3:
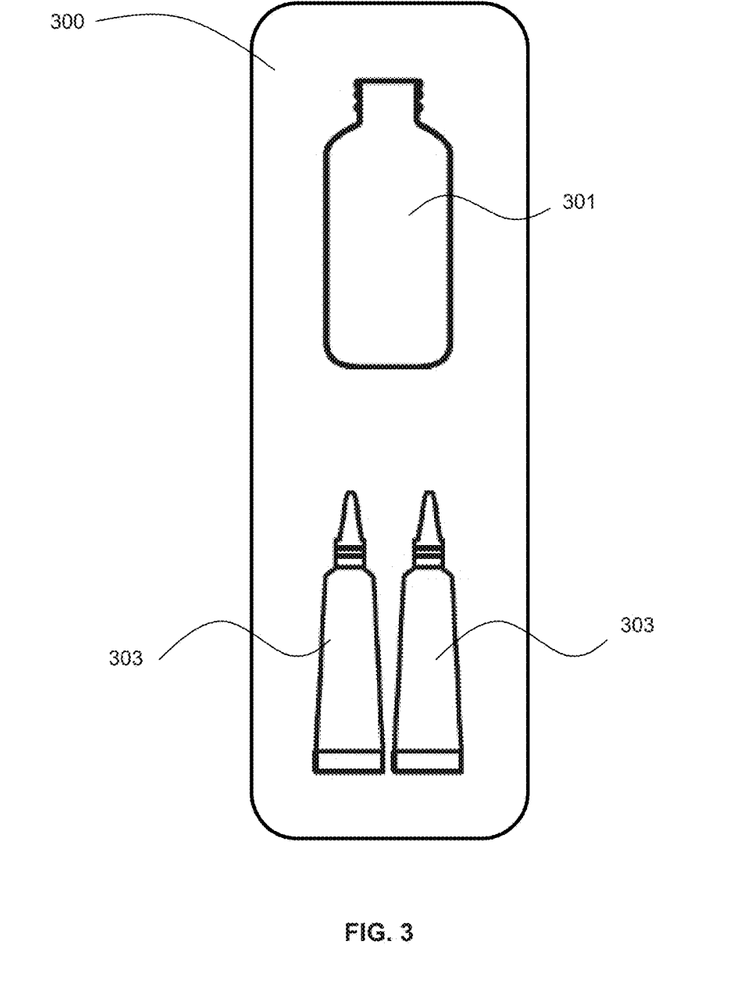
FIG. 3 is a skin care system, according to an embodiment of the present disclosure.

As shown in FIG. 1, after the booster compositions are determined and the base oil composition is provided, the booster compositions and oil base formulations are individually assembled into a kit or system including the selected boosters and base oil (step 109). FIG. 3 shows an exemplary configuration of a skin care system 300, according to an embodiment of the present disclosure. The packaging and system are configured to permit mixing of the booster compositions 303 and the base oil composition 301 at home with simple agitation. For example, the base oil composition 301 includes sufficient space in the packaging to receive the booster composition 303 and to permit agitation, such as by shaking the container. Ophthalmic tip tubes, for example, may help consumer mix boosters into primary dropper containing base. The co-solubilized booster composition 303 readily disperses into the base oil composition to form a treatment composition.

The following examples are intended to further illustrate the present invention. They are not intended to limit the invention in any way. Unless otherwise indicated, all parts are by weight.

EXAMPLES

Example 1

TABLE 1

| INGREDIENT | Base Oil |
|---|---|
| EMOLLIENTS | 44 |
| SQUALANE | 35 |
| BOTANICAL OILS | 20 |
| ANTIOXIDANTS | 1 |
| Total | 100 |

TABLE 2

| INGREDIENT | Wrinkle Reducing Booster | Brightening Booster | Pore Minimizing Booster | Texture Refining Booster | Visible Redness Neutralizing Booster |
|---|---|---|---|---|---|
| CAPRYLOYL SALICYLIC ACID | 0.6 | 0.6 | 0.6 | 1.2 | |
| PHENYLETHYL RESORCINOL | | 3 | | | |
| ESSENTIAL OILS | 0.7 | 1.2 | 1.2 | 0.6 | |
| EMOLLIENTS | 32.2 | 9.2 | 8 | 30.2 | 32 |
| SQUALANE | 35 | 35 | 35 | 35 | 35 |
| BOTANICAL OILS | 20 | 20 | 20 | 20 | 20 |
| SALICYLIC ACID | | | 1.2 | | |
| CRITHMUM MARITIMUM EXTRACT* | | | 3 | | |
| HELIANTHUS ANNUUS (SUNFLOWER) SEED OIL UNSAPONIFIABLES | | | | | 12 |
| GLYCERYL LINOLEATE (and) GLYCERYL OLEATE (and) GLYCERYL LINOLENATE | | | | 12 | |
| ANTIOXIDANTS | 1 | 1 | 1 | 1 | 1 |
| RETINYL PALMITATE (and) HELIANTHUS ANNUUS (SUNFLOWER) SEED OIL** | 1.5 | | | | |
| RETINOL*** | 9 | | | | |
| ASCORBYL TETRAISOPALMITATE | | 30 | 30 | | |
| Total | 100 | 100 | 100 | 100 | 100 |

*Includes 4% Active *Crithimum Maritimum* Extract
**Include 55% Active Retinyl Palmitate
***Includes 10% Active Retinol Example 1 shows various range of compositions which allow for solubility of high levels of actives in the boosters and allow for good co-solubility of base and boosters.

TABLE 1 shows effective composition of base oil. TABLE 2 shows effective composition of boosters. The inventive examples in TABLE 1 and 2 show various ranges of compositions which allow for solubility of high levels of actives in the boosters and allow for good co-solubility of base and boosters.

Comparative Example 1

TABLE 3

| INGREDIENT | Base Oil |
|---|---|
| EMOLLIENTS | 89.9 |
| SQUALANE | 5 |
| BOTANICAL OILS | 5 |
| ANTIOXIDANTS | 0.1 |
| Total | 100 |

TABLE 4

| INGREDIENT | Wrinkle Reducing Booster | Brightening Booster | Pore Minimizing Booster | Texture Refining Booster | Visible Redness Neutralizing Booster |
|---|---|---|---|---|---|
| CAPRYLOYL SALICYLIC ACID | 5 | 5 | 5 | 10 | |
| PHENYLETHYL RESORCINOL | | 0.1 | | | |
| ESSENTIAL OILS | 0.1 | 0.1 | 0.1 | 0.1 | |
| EMOLLIENTS | 84.6 | 79.7 | 54.8 | 78.8 | 88.9 |
| SQUALANE | 5 | 5 | 5 | 5 | 5 |
| BOTANICAL OILS | 5 | 5 | 5 | 5 | 5 |
| SALICYLIC ACID | | | 5 | | |
| *CRITHMUM MARITIMUM* EXTRACT* | | | 10 | | |
| *HELIANTHUS ANNUUS* (SUNFLOWER) SEED OIL UNSAPONIFIABLES | | | | | 1 |
| GLYCERYL LINOLEATE (and) GLYCERYL OLEATE (and) GLYCERYL LINOLENATE | | | | 1 | |
| ANTIOXIDANTS | 0.1 | 0.1 | 0.1 | 0.1 | 0.1 |
| RETINYL PALMITATE (and) *HELIANTHUS ANNUUS* (SUNFLOWER) SEED OIL** | 0.1 | | | | |
| RETINOL*** | 0.1 | | | | |
| ASCORBYL TETRAISOPALMITATE | | 5 | 5 | | |
| Total | 100 | 100 | 100 | 100 | 100 |

*Includes 4% Active *Crithimum Maritimum* Extract
**Include 55% Active Retinyl Palmitate
***Includes 10% Active Retinol Comparative Example 1 shows various range of compositions that would not be effective For example, deficiencies of this comparative example include compositions with active levels that are beyond the solubility limit of the formulation as well as active levels that are so low that they do not provide efficacious results to the consumer.

Example 2

TABLE 5

| INGREDIENT | Base Oil |
|---|---|
| EMOLLIENTS | 48 |
| SQUALANE | 25 |
| BOTANICAL OILS | 25 |
| ANTIOXIDANTS | 2 |
| Total | 100 |

TABLE 6

| INGREDIENT | Wrinkle Reducing Booster | Brightening Booster | Pore Minimizing Booster | Texture Refining Booster | Visible Redness Neutralizing Booster |
|---|---|---|---|---|---|
| CAPRYLOYL SALICYLIC ACID | 1 | 1 | 1 | 1.5 | |
| PHENYLETHYL RESORCINOL | | 5 | | | |
| ESSENTIAL OILS | 1.1 | 1 | 0.9 | 0.5 | |
| EMOLLIENTS | 30 | 13 | 10.1 | 26 | 28 |
| SQUALANE | 25 | 25 | 25 | 25 | 25 |

TABLE 6-continued

| INGREDIENT | Wrinkle Reducing Booster | Brightening Booster | Pore Minimizing Booster | Texture Refining Booster | Visible Redness Neutralizing Booster |
|---|---|---|---|---|---|
| BOTANICAL OILS | 25 | 25 | 25 | 25 | 25 |
| SALICYLIC ACID | | | 0.75 | | |
| CRITHMUM MARITIMUM EXTRACT* | | | 1.25 | | |
| HELIANTHUS ANNUUS (SUNFLOWER) SEED OIL UNSAPONIFIABLES | | | | | 20 |
| GLYCERYL LINOLEATE (and) GLYCERYL OLEATE (and) GLYCERYL LINOLENATE | | | | 20 | |
| ANTIOXIDANTS | 2 | 2 | 2 | 2 | 2 |
| RETINYL PALMITATE (and) HELIANTHUS ANNUUS (SUNFLOWER) SEED OIL** | 0.9 | | | | |
| RETINOL*** | 15 | | | | |
| ASCORBYL TETRAISOPALMITATE | | 28 | 34 | | |
| Total | 100 | 100 | 100 | 100 | 100 |

*Includes 4% Active *Crithimum Maritimum* Extract
**Include 55% Active Retinyl Palmitate
***Includes 10% Active Retinol Example 2 shows various range of compositions which allow for solubility of high levels of actives in the boosters and allow for good co-solubility of base and boosters.

TABLE 5 shows effective composition of base oil. TABLE 6 shows effective composition of boosters. The inventive examples in TABLE 5 and 6 show various ranges of compositions which allow for solubility of high levels of actives in the boosters and allow for good co-solubility of base and boosters.

Example 3

TABLE 7

| INGREDIENT | Base Oil |
|---|---|
| EMOLLIENTS | 49 |
| SQUALANE | 20 |
| BOTANICAL OILS | 30 |
| ANTIOXIDANTS | 1 |
| Total | 100 |

TABLE 8

| INGREDIENT | Wrinkle Reducing Booster | Brightening Booster | Pore Minimizing Booster | Texture Refining Booster | Visible Redness Neutralizing Booster |
|---|---|---|---|---|---|
| CAPRYLOYL SALICYLIC ACID | 0.5 | 0.5 | 0.5 | 1 | |
| PHENYLETHYL RESORCINOL | | 1 | | | |
| ESSENTIAL OILS | 0.5 | 0.8 | 1.4 | 0.9 | |
| EMOLLIENTS | 40.3 | 12.7 | 10.85 | 37.1 | 39 |
| SQUALANE | 20 | 20 | 20 | 20 | 20 |
| BOTANICAL OILS | 30 | 30 | 30 | 30 | 30 |
| SALICYLIC ACID | | | 2 | | |
| CRITHMUM MARITIMUM EXTRACT* | | | 6.25 | | |
| HELIANTHUS ANNUUS (SUNFLOWER) SEED OIL UNSAPONIFIABLES | | | | | 10 |
| GLYCERYL LINOLEATE (and) GLYCERYL OLEATE (and) GLYCERYL LINOLENATE | | | | 10 | |
| ANTIOXIDANTS | 1 | 1 | 1 | 1 | 1 |
| RETINYL PALMITATE (and) HELIANTHUS ANNUUS (SUNFLOWER) SEED OIL** | 2.7 | | | | |

TABLE 8-continued

| INGREDIENT | Wrinkle Reducing Booster | Brightening Booster | Pore Minimizing Booster | Texture Refining Booster | Visible Redness Neutralizing Booster |
|---|---|---|---|---|---|
| RETINOL*** | 5 | | | | |
| ASCORBYL TETRAISOPALMITATE | | 34 | 28 | | |
| Total | 100 | 100 | 100 | 100 | 100 |

*Includes 4% Active *Crithimum Maritimum* Extract
**Include 55% Active Retinyl Palmitate
***Includes 10% Active Retinol Example 3 shows various range of compositions which allow for solubility of high levels of actives in the boosters and allow for good co-solubility of base and boosters.

TABLE 7 shows effective composition of base oil. TABLE 8 shows effective composition of boosters. The inventive examples in TABLE 7 and 8 show various ranges of compositions which allow for solubility of high levels of actives in the boosters and allow for good co-solubility of base and boosters.

TABLE 9

| INCI US | Loading (wt %) | | | |
|---|---|---|---|---|
| Salicylic Acid | 3% | 5%* | 10%*15%* | |
| Caprylyl Salicylic Acid | 3% | 5%* | 10%*15%* | |
| Phenylethyl Resorcinol | 5% | 10% | 15% | — |
| Ascorbyl Tetraisopalmitate | 40% | 50% | 60% | — |
| *Crithmum Martimum* Extract (4% Active) | 5% | 10%* | 15%* | — |
| Retinol (10% Active) | 10% | 20% | 30% | — |
| Retinyl Palmitate (and) *Helianthus Annuus* Seed Oil (55% Active) | 5% | 10% | 20% | — |
| Glyceryl Linoleate (and) Glyceryl Oleate (and) Glyceryl Linolenate | 15% | 20% | 40% | — |

*Insoluble

TABLE 9 shows solubility of active ingredients in base oil composition.

TABLE 10

| INGREDIENT | Base with Wrinkle Reducing and Brightening Booster from Example 1 | Base with Pore and Texture Booster from Example 2 | Base with Visible Redness Neutralizing Booster and Texture Booster from Example 3 |
|---|---|---|---|
| CAPRYLOYL SALICYLIC ACID | 0.2 | 0.42 | 0.17 |
| PHENYLETHYL RESORCINOL | 0.5 | | |
| ESSENTIAL OILS | 0.32 | 0.23 | 0.15 |
| EMOLLIENTS | 36.23 | 38.00 | 45.34 |
| SQUALANE | 35 | 25 | 20 |
| BOTANICAL OILS | 20 | 25 | 30 |
| SALICYLIC ACID | | 0.13 | |
| *CRITHMUM MARITIMUM* EXTRACT* | | 0.21 | |
| *HELIANTHUS ANNUUS* (SUNFLOWER) SEED OIL UNSAPONIFIABLES | | | 1.67 |
| GLYCERYL LINOLEATE (and) GLYCERYL OLEATE | | 3.34 | 1.67 |
| (and) GLYCERYL LINOLENATE ANTIOXIDANTS | 1 | 2 | 1 |
| RETINYL PALMITATE (and) *HELIANTHUS ANNUUS* (SUNFLOWER) SEED OIL** | 0.25 | | |
| RETINOL*** | 1.50 | | |
| ASCORBYL TETRAISOPALMITATE | 5.00 | 5.67 | |
| Total | 100 | 100 | |

TABLE 10 shows an exemplary chart of booster+base combinations.

Summary of Clinical/Consumer testing:

An instrumental evaluation of the effectiveness in improving skin hydration and maintaining skin barrier function was carried out on the base oil formulation. Under the conditions of the study, the oil elicited statistically significant improvements in skin barrier function when compared to the baseline and statistically significant improvements in skin hydration when compared to the baseline.

TABLE 11

Skin Strengthening Concentrate-Clinical Instrumental Testing

| Claim | Assessment |
|---|---|
| Improvement in skin barrier function (TEWL) | X |
| Improvement in skin hydration | X |

"X" indicates statistically significant improvement at later time point when compared to baseline ($p < 0.05$)

Clinical evaluations were conducted on representative formulas containing each booster; formula compositions consisted of the base oil and the booster complex in the ratio 5:1. Various skin attributes of the representative formulas were evaluated via by an expert grader both initially and at later time points. Under the conditions of the study, results show a statistically significant improvement in attributes of the skin over time vs. baseline for all booster representative formulas.

TABLE 12

| | Attribute | Assessment |
|---|---|---|
| Brightening Complex | Improvement in skin radiance/brightness/luminosity | X |
| | Improvement in skin tone evenness | X |
| | Improvement in overall appearance of skin quality | X |
| Wrinkle Reducing Complex | Improvement in appearance of Fine Lines | X |
| | Improvement in appearance of Wrinkles | X |
| | Improvement in Overall Appearance of Skin Quality | X |
| Texture Refining Complex | Improvement in the appearance of skin smoothness (visual) | X |
| | Improvements in skin texture/smoothness (tactile) | X |
| | Improvement in overall appearance of skin quality (visual) | X |
| Pore Minimizing Complex | Improvement in Pore Size Appearance | X |
| | Improvement in Appearance of Shine | X |
| | Improvement in Overall Skin Appearance | X |
| Visible Redness Neutralizing Complex | Improvement in Skin Redness/Red Patches | X |
| | Improvement in Overall Skin Appearance | X |

"X" indicates statistically significant improvement at later time point when compared to baseline ($p < 0.05$)

Consumer home-use testing was carried out on all formula combinations consisting of the base oil mixed with two different targeted booster complexes. The objective of these studies was to evaluate consumer perception of the various attributes of the oil products immediately following initial usage, and after two and four weeks of use. Results indicate that the oil products are well appreciated by the consumer both aesthetically and in perceived efficacy.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A skin care system comprising:
  (a) an anhydrous base oil composition disposed in a base oil composition container, the base oil composition comprising squalane; and
  (b) a plurality of anhydrous booster compositions and a plurality of booster composition containers, each of the plurality of booster compositions disposed separately in its own booster composition container, each of the plurality of booster compositions being readily dispersible into the base oil composition, the plurality of booster compositions comprising corresponding active ingredients, each of the corresponding active ingredients corresponding to treatment skin conditions determined by a consumer,
  wherein the base oil composition container includes space sufficient to contain the base oil composition and to receive the plurality of booster compositions, and the base oil composition container is arranged and disposed for mixing therein the plurality of booster compositions with the base oil composition to form a treatment composition dispersible from the base oil composition container; and
  wherein the treatment skin conditions include at least two conditions selected from the group consisting of skin brightness, skin lines, skin wrinkles, visibility of pores, skin texture, skin redness, skin firmness, and skin tone evenness; and
  wherein the booster composition corresponding to one or more of skin brightness and skin tone evenness includes greater than about 25% brightening booster active, based upon the weight of the booster composition; and
  wherein the booster composition corresponding to one or more of skin wrinkles, skin lines and skin firmness includes greater than about 0.5% wrinkle reducing booster active, based upon the weight of the booster composition; and
  wherein the booster composition corresponding to visibility of pores includes greater than about 25% pore minimizing booster active, based upon the weight of the booster composition; and
  wherein the booster composition corresponding to skin texture includes greater than about 7.5% texture refining booster active, based upon the weight of the booster composition; and
  wherein the booster composition corresponding to skin redness includes greater than about 7.5% visible redness booster active, based upon the weight of the booster composition.

2. The skin care system of claim 1, the base oil composition container is a dropper container and the plurality of booster composition containers are ophthalmic tip tubes.

3. The skin care system of claim 1, wherein the volume of the base oil composition container is sufficient for mixing the base oil composition and the plurality of booster compositions by manual agitation.

4. The skin care system of claim 1, wherein each of the plurality of booster compositions is compatible with the base composition.

5. The skin care system of claim 4, each of the plurality of booster compositions is pre-solubilized with one or more ingredients also present in the base oil composition.

6. The skin care system of claim 5, wherein each of the plurality of booster compositions includes squalane.

7. The skin care system of claim 1, wherein the system comprises two booster compositions, each corresponding to dissimilar treatment skin conditions.

8. The skin care system of claim 1, wherein the active ingredients corresponding to one or more of skin brightness and skin tone evenness include at least one active ingredient selected from the group consisting of ascorbyl tetraisopalmitate, phenylethyl resorcinol, arbutin, eperua falcata bark extract, ceramides, punica granatum fruit extract, citrus aurantium dulcis (orange) peel essential oil, rapeseed oil, cassia alata leaf extract, purple rice extract, and combinations thereof.

9. The skin care system of claim 8, wherein the greater than about 25% brightening booster active includes at least one active ingredient selected from the group consisting of arbutin, eperua falcata bark extract, ceramides, punica granatum fruit extract, citrus aurantium dulcis (orange) peel essential oil, rapeseed oil, cassia alata leaf extract, purple rice extract, and combinations thereof, wherein ascorbyl tetraisopalmitate, when present, is present at greater than about 27%, based upon the weight of the booster composition, together with phenylethyl resorcinol present at greater than about 1%, based upon the weight of the booster composition.

10. The skin care system of claim 1, wherein the active ingredients corresponding to one or more of skin wrinkles, skin lines and skin firmness include at least one active ingredient selected from the group consisting of retinol, retinyl palmitate, punica granatum fruit extract, pelargonium graveolens flower oil, melissa officinalis leaf oil, zingiber officinale (ginger) root oil, theobroma cacao (cocoa) extract, purple rice extract, phytosphingosine, cinnamic acid, and combinations thereof.

11. The skin care system of claim 10, wherein the greater than about 0.5% wrinkle reducing booster active includes at least one active ingredient selected from the group consisting of retinol, retinyl palmitate, punica granatum fruit extract, pelargonium graveolens flower oil, melissa officinalis leaf oil, zingiber officinale (ginger) root oil, theobroma cacao (cocoa) extract, purple rice extract, phytosphingosine, cinnamic acid, and combinations thereof, wherein retinol, when present, is present at greater than about 25%, based upon the weight of the booster composition together with retinyl palmitate present at greater than about 25%, based upon the weight of the booster composition.

12. The skin care system of claim 1, wherein the active ingredients corresponding to visibility of pores include at least one active ingredient selected from the group consisting of ascorbyl tetraisopalmitate, salicylic acid, crithimum maritimum extract, totarol, ulkenia amoeboidea oil, and combinations thereof.

13. The skin care system of claim 12, wherein the greater than about 25% pore minimizing booster active includes at least one active ingredient selected from the group consisting of ascorbyl tetraisopalmitate, salicylic acid, crithimum maritimum extract, totarol, ulkenia amoeboidea oil, and combinations thereof, wherein ascorbyl tetraisopalmitate, when present, is present at greater than about 27%, based upon the weight of the booster composition together with salicylic acid present at greater than about 0.5%, based upon the weight of the booster composition, and crithimum maritimum extract present at greater than about 0.05%, based upon the weight of the booster composition.

14. The skin care system of claim 1, wherein the active ingredients corresponding to skin texture include at least one active ingredient selected from the group consisting of glyceryl linoleate (and) glyceryl oleate (and) glyceryl linolenate, punica granatum fruit extract, shea butter, rice bran oil, safflower oil, phospholipids, panax ginseng root extract, and combinations thereof.

15. The skin care system of claim 1, wherein the active ingredients corresponding to skin redness include at least one active ingredient selected from the group consisting of helianthus annuus (sunflower) seed oil unsaponifiables, melissa officinalis leaf oil, zingiber officinale (ginger) root oil, anthemis nobilis flower oil, and combinations thereof.

16. The skin care system of claim 1, wherein the base oil composition comprises at least components selected from the group consisting of squalane, botanical oil, hexyldecanol, and tocopherol, octyldodecanol, dicaprylyl ether, zea mays (corn) oil, passiflora edulis seed oil, oryza sativa (rice) bran oil, and combinations thereof.

17. The skin care system of claim 1, wherein the base oil composition, the booster compositions and the treatment composition are oil based compositions.

18. The skin care system of claim 1, wherein each of the plurality of booster compositions includes one or more of squalane, capryloyl salicylic acid and botanical oils.

19. The skin care system of claim 1, wherein the base oil composition includes squalane present at greater that about 20%, based upon the weight of the base oil composition, and one or more of the plurality of booster compositions includes squalane present at greater than about 20%, based upon the weight of the booster composition.

20. A skin care system comprising:
(a) an anhydrous base oil composition disposed in a base oil composition container, the base oil composition comprising squalane; and
(b) a plurality of anhydrous booster compositions and a plurality of booster composition containers, each of the plurality of booster compositions disposed separately in its own booster composition container, each of the plurality of booster compositions being readily dispersible into the base oil composition, the plurality of booster compositions comprising corresponding active ingredients, each of the corresponding active ingredients corresponding to treatment skin conditions selected from the group consisting of skin brightness, skin lines, skin wrinkles, visibility of pores, skin texture, skin redness, skin firmness, and skin tone evenness,
wherein the base oil composition container includes space sufficient to contain the base oil composition and to receive the plurality of booster compositions, and the base oil composition container is arranged and disposed for mixing therein the plurality of booster compositions with the base oil composition to form a treatment composition dispersible from the base oil composition container.

21. The skin care system of claim 20, wherein the base oil comprises squalane in a concentration comprising greater than about 20 weight percent by weight of total composition.

22. The skin care system of claim 20, wherein the base oil comprises at least components selected from the group consisting of botanical oil, hexyldecanol, and tocopherol, octyldodecanol, dicaprylyl ether, zea mays (corn) oil, passiflora edulis seed oil, oryza sativa (rice) bran oil, and combinations thereof.

23. The skin care system of claim 20, wherein the at least one active ingredient corresponding to skin brightness includes at least one active ingredient selected from the group consisting of ascorbyl tetraisopalmitate, phenylethyl resorcinol, arbutin, eperua falcata bark extract, ceramides, punica granatum fruit extract, citrus aurantium dulcis (orange) peel essential oil, rapeseed oil, cassia alata leaf extract, purple rice extract, and combinations thereof.

24. The skin care system of claim 20, wherein the at least one active ingredient corresponding to skin wrinkles includes at least one active ingredient selected from the group consisting of retinol, retinyl palmitate, punica granatum fruit extract, pelargonium graveolens flower oil, melissa officinalis leaf oil, zingiber officinale (ginger) root oil, theobroma cacao (cocoa) extract, purple rice extract, phytosphingosine, cinnamic acid, and combinations thereof.

25. The skin care system of claim 20, wherein the at least one active ingredient corresponding to visibility of pores includes at least one active ingredient selected from the group consisting of ascorbyl tetraisopalmitate, salicylic acid, crithimum maritimum extract, totarol, ulkenia amoeboidea oil, and combinations thereof.

26. The skin care system of claim 20, wherein the at least one active ingredient corresponding to skin texture includes at least one active ingredient selected from the group consisting of glyceryl linoleate (and) glyceryl oleate (and) glyceryl linolenate, punica granatum fruit extract, shea butter, rice bran oil, safflower oil, phospholipids, panax ginseng root extract, and combinations thereof.

27. The skin care system of claim 20, wherein the at least one active ingredient corresponding to skin redness includes at least one active ingredient selected from the group consisting of helianthus annuus (sunflower) seed oil unsaponifiables, melissa officinalis leaf oil, zingiber officinale (ginger) root oil, anthemis nobilis flower oil, and combinations thereof.

28. The skin care system of claim 20, wherein the booster compositions comprise squalane.

29. The skin care system of claim 20, wherein the booster compositions comprise squalane in a concentration comprising greater than about 20 weight percent by weight of total composition.

30. A method for forming a skin care composition, the method comprising:
  providing an anhydrous base oil composition disposed in a base oil composition container, the base oil composition comprising squalane;
  providing a plurality of anhydrous booster compositions, each of the plurality of booster compositions being separately contained and each comprising corresponding active ingredients, the corresponding active ingredients corresponding to treatment skin conditions selected from the group consisting of skin brightness, skin lines, skin wrinkles, visibility of pores, skin texture, skin redness, skin firmness, and skin tone evenness;
  dispensing into and mixing within the base oil composition container two or more booster compositions corresponding to treatment skin conditions selected from the plurality of booster compositions.

31. A method for forming a skin care composition, the method comprising:
  (a) providing a skin care system comprising:
    (i) an anhydrous base oil composition disposed in a base oil composition container, the base oil composition comprising squalane, the base oil composition container including space sufficient to contain the base oil composition and to receive a plurality of booster compositions, and the base oil composition container arranged and disposed for mixing therein the plurality of booster compositions with the base oil composition to form a treatment composition dispersible from the base oil composition container;
    (ii) a plurality of anhydrous booster compositions and a plurality of booster composition containers, each of the plurality of booster compositions disposed separately in its own booster composition container, each of the plurality of booster compositions being readily dispersible into the base oil composition, the plurality of booster compositions comprising corresponding active ingredients, each of the corresponding active ingredients corresponding to treatment skin conditions determined by a consumer; wherein the treatment skin conditions include at least two conditions selected from the group consisting of skin brightness, skin lines, skin wrinkles, visibility of pores, skin texture, skin redness, skin firmness, and skin tone evenness; and wherein the booster composition corresponding to one or more of skin brightness and skin tone evenness includes greater than about 25% brightening booster active, based upon the weight of the booster composition; and wherein the booster composition corresponding to one or more of skin wrinkles, skin lines and skin firmness includes greater than about 0.5% wrinkle reducing booster active, based upon the weight of the booster composition; and wherein the booster composition corresponding to visibility of pores includes greater than about 25% pore minimizing booster active, based upon the weight of the booster composition; and wherein the booster composition corresponding to skin texture includes greater than about 7.5% texture refining booster active, based upon the weight of the booster composition; and wherein the booster composition corresponding to skin redness includes greater than about 7.5% visible redness booster active, based upon the weight of the booster composition;
  (b) disposing the plurality of booster compositions into the base oil composition container; and
  (c) mixing the plurality of booster compositions.

32. A method of imparting skin treatment benefits onto skin by applying the composition of claim 1 onto skin.

* * * * *